United States Patent
Shin et al.

(10) Patent No.: US 11,771,647 B2
(45) Date of Patent: Oct. 3, 2023

(54) EYE DROPS IN FORM OF SOLUTION COMPRISING BENZOPYRAN DERIVATIVE OR PHARMACEUTICALLY ACCEPTABLE SALT THEREOF

(71) Applicant: HANLIM PHARMACEUTICAL CO., LTD., Yongin-si (KR)

(72) Inventors: Dong-Yeop Shin, Gunpo-si (KR); Hu-Seong Kim, Ansan-si (KR); Geun-Hyeog Lee, Yongin-si (KR); Kyung-Joon Kim, Yongin-si (KR); Yun-Seok Cho, Suwon-si (KR); Mi-Jin O, Suwon-si (KR); Mi-Jung Kim, Seoul (KR)

(73) Assignee: HANLIM PHARMACEUTICAL CO., LTD., Yongin-si (KR)

( * ) Notice: Subject to any disclaimer, the term of this patent is extended or adjusted under 35 U.S.C. 154(b) by 694 days.

(21) Appl. No.: 16/975,695

(22) PCT Filed: Feb. 18, 2019

(86) PCT No.: PCT/KR2019/001894
§ 371 (c)(1),
(2) Date: Aug. 25, 2020

(87) PCT Pub. No.: WO2019/168289
PCT Pub. Date: Sep. 6, 2019

(65) Prior Publication Data
US 2020/0405634 A1      Dec. 31, 2020

(30) Foreign Application Priority Data

Feb. 28, 2018   (KR) .................. 10-2018-0024470

(51) Int. Cl.
| | | |
|---|---|---|
| *A61K 9/00* | (2006.01) | |
| *A61P 27/02* | (2006.01) | |
| *A61K 9/08* | (2006.01) | |
| *A61K 31/4178* | (2006.01) | |
| *A61K 47/02* | (2006.01) | |
| *A61K 47/10* | (2017.01) | |
| *A61K 47/18* | (2017.01) | |

(52) U.S. Cl.
CPC .............. *A61K 9/0048* (2013.01); *A61K 9/08* (2013.01); *A61K 31/4178* (2013.01); *A61K 47/02* (2013.01); *A61K 47/10* (2013.01); *A61K 47/183* (2013.01); *A61K 47/186* (2013.01); *A61P 27/02* (2018.01)

(58) Field of Classification Search
CPC .... A61K 9/0048; A61K 9/08; A61K 31/4178; A61K 47/02; A61K 47/10; A61K 47/183; A61K 47/186; A61P 27/02
See application file for complete search history.

(56) References Cited

U.S. PATENT DOCUMENTS

| | | |
|---|---|---|
| 5,856,345 A | 1/1999 | Doi et al. |
| 6,274,609 B1 | 8/2001 | Yasueda et al. |
| 7,279,497 B2 | 10/2007 | Yi et al. |
| 2005/0267188 A1 | 12/2005 | Yi et al. |
| 2014/0018402 A1* | 1/2014 | Yi ..................... A61K 31/4178 |
| | | 514/397 |
| 2015/0031705 A1 | 1/2015 | Horn |
| 2015/0320782 A1 | 11/2015 | Panjwani et al. |

* cited by examiner

*Primary Examiner* — Michael Barker
*Assistant Examiner* — Jed A Kucharczk
(74) *Attorney, Agent, or Firm* — Vorys, Sater, Seymour and Pease LLP; Mih Suhh Koh

(57) ABSTRACT

The present invention provides an eye drop formulation in the form of a solution, comprising (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof; propylene glycol as a stabilizing agent; and a pH controlling agent in an aqueous medium, wherein the eye drop formulation has a pH ranging from 4.0 to 5.0. The eye drop formulation of the present invention can contain (2R,3R,4S)-6-amino-4-[N-(4-chlorophenyl)-N-(1H-imidazol-2-yl-methyl)amino]-3-hydroxy-2-methyl-2-dimethoxymethyl-3,4-dihydro-2H-1-benzopyran or a pharmaceutically acceptable salt thereof in a high concentration; and has an excellent stability. In addition, the pharmaceutical product for preventing or treating macular degeneration according to the present invention can be stored for extended periods.

17 Claims, 2 Drawing Sheets

EYE DROPS IN FORM OF SOLUTION COMPRISING BENZOPYRAN DERIVATIVE OR PHARMACEUTICALLY ACCEPTABLE SALT THEREOF

TECHNICAL FIELD

The present invention relates to an eye drop formulation in the form of a solution comprising benzopyran derivative or a pharmaceutically acceptable salt thereof. More specifically, the present invention relates to an eye drop formulation in the form of a solution not only comprising benzopyran derivative or a pharmaceutically acceptable salt thereof and a specific stabilizing agent; but also having a specific pH range.

BACKGROUND ART

The benzopyran derivative of Formula 1, whose chemical name is (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran, is known as a compound having therapeutic effects for cancer, rheumatoid arthritis, etc. (Korean Patent No. 10-0492252).

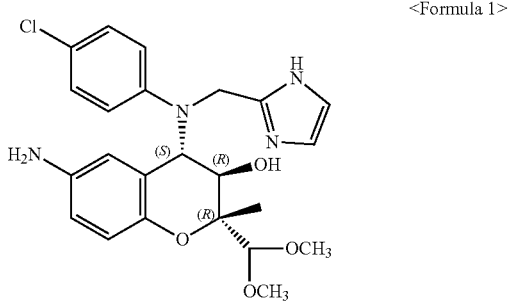

<Formula 1>

And also, the compound of Formula 1 can be prepared as an eye drop formulation based on a low-molecular weight material; and usefully applied to the prevention and treatment of macular degeneration, without injecting directly into the affected site as in the antibody injection therapy (Korean Laid-open Patent Publication No. 10-2012-0112162). Korean Laid-open Patent Publication No. 10-2012-0112162 discloses an eye drop formulation in the form of a solution or a suspension. For example, Korean Laid-open Patent Publication No. 10-2012-0112162 discloses eye drop formulations in the form of a solution containing the compound of Formula 1 in the concentrations of 0.06 w/v % and 0.09 w/v %, which are prepared by using polyethylene glycol and glycerine as a solubilizer.

Meanwhile, for effective treatment of macular degeneration, an eye drop formulation in the form of a solution containing the compound of Formula 1 in a high concentration, for example, in a concentration of 0.3 w/v % or more (i.e., in a concentration of 3.0 mg/ml or more) is required. However, since the compound of Formula 1 is a poorly water-soluble material, the eye drop formulation in the form of a solution disclosed in Korean Laid-open Patent Publication No. 10-2012-0112162 has a problem that the compound of Formula 1 cannot be dissolved in a high concentration of 3.0 mg/ml or more. In addition, the compound of Formula 1 has low stability in an aqueous medium. Thus, when the compound of Formula 1 is contained in a high concentration of 3.0 mg/ml or more, there is a problem that generation of the degradation products is highly increased.

DISCLOSURE

Technical Problem

The present inventors carried out various researches in order to develop an eye drop formulation in the form of a solution not only containing the compound of Formula 1 in a high concentration (for example, in a concentration of 3.0 mg/ml or more) in an aqueous medium but also having improved stability. As the results thereof, the present inventors have found that, by performing formulation processes through controlling the pH of the solution to a specific range (i.e., pH 4.0 to pH 5.0) and using a specific stabilizing agent (i.e., propylene glycol), it is possible to prepare an eye drop formulation in the form of a solution containing the compound of Formula 1 in a high concentration and having an excellent stability. In addition, the present inventors have found that, when the resulting eye drop formulation is filled in a light-shielding container, it is possible to obtain a pharmaceutical product that can be stored for extended periods.

Therefore, it is an object of the present invention to provide an eye drop formulation in the form of a solution, comprising the compound of Formula 1 or a pharmaceutically acceptable salt thereof; and propylene glycol as a stabilizing agent, wherein the eye drop formulation has a pH ranging from 4.0 to 5.0.

It is another object of the present invention to provide a pharmaceutical product for preventing or treating macular degeneration which is obtained by filling the eye drop formulation into a light-shielding container.

Technical Solution

In accordance with an aspect of the present invention, there is provided an eye drop formulation in the form of a solution, comprising (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof; propylene glycol as a stabilizing agent; and a pH controlling agent in an aqueous medium, wherein the eye drop formulation has a pH ranging from 4.0 to 5.0.

In the eye drop formulation of the present invention, the (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof may be present in a concentration of 3 mg/ml or more, preferably in a concentration ranging from 3 to 10 mg/ml. And, the propylene glycol may be present in a concentration ranging from 1 to 20 mg/ml, preferably from 5 to 17 mg/ml, more preferably from 10 to 15 mg/ml. The eye drop formulation of the present invention may have preferably a pH ranging from 4.2 to 4.7, more preferably a pH of about 4.5.

The eye drop formulation of the present invention may further comprise one or more excipients selected from the group consisting of an auxiliary stabilizing agent, a buffering agent, and a preservative. The auxiliary stabilizing agent may be one or more selected from the group consisting of ethylenediaminetetraacetic acid or a salt thereof and tromethamine. The buffering agent may be one or more selected from the group consisting of borax, boric acid, a phosphate salt, citric acid, sodium citrate, and aminocaproic acid. The preservative may be one or more selected from the group consisting of benzalkonium chloride, chlorhexidine gluconate, sorbic acids, chlorobutanol, and parabens.

In accordance with another aspect of the present invention, there is provided a pharmaceutical product for preventing or treating macular degeneration which is obtained by filling the eye drop formulation into a light-shielding container. Preferably, the pharmaceutical product for preventing or treating macular degeneration according to the present invention may be obtained by filling the eye drop formulation into a light-shielding container and then packing the resulting product in a paper case.

Advantageous Effects

The eye drop formulation in the form of a solution according to the present invention can contain the compound of Formula 1 in a high concentration and also has an excellent stability. In addition, the pharmaceutical product according to the present invention can be stored for extended periods. Therefore, the eye drop formulation in the form of a solution and the pharmaceutical product according to the present invention can be usefully used for preventing or treating macular degeneration.

BEST MODE

Figure 1:
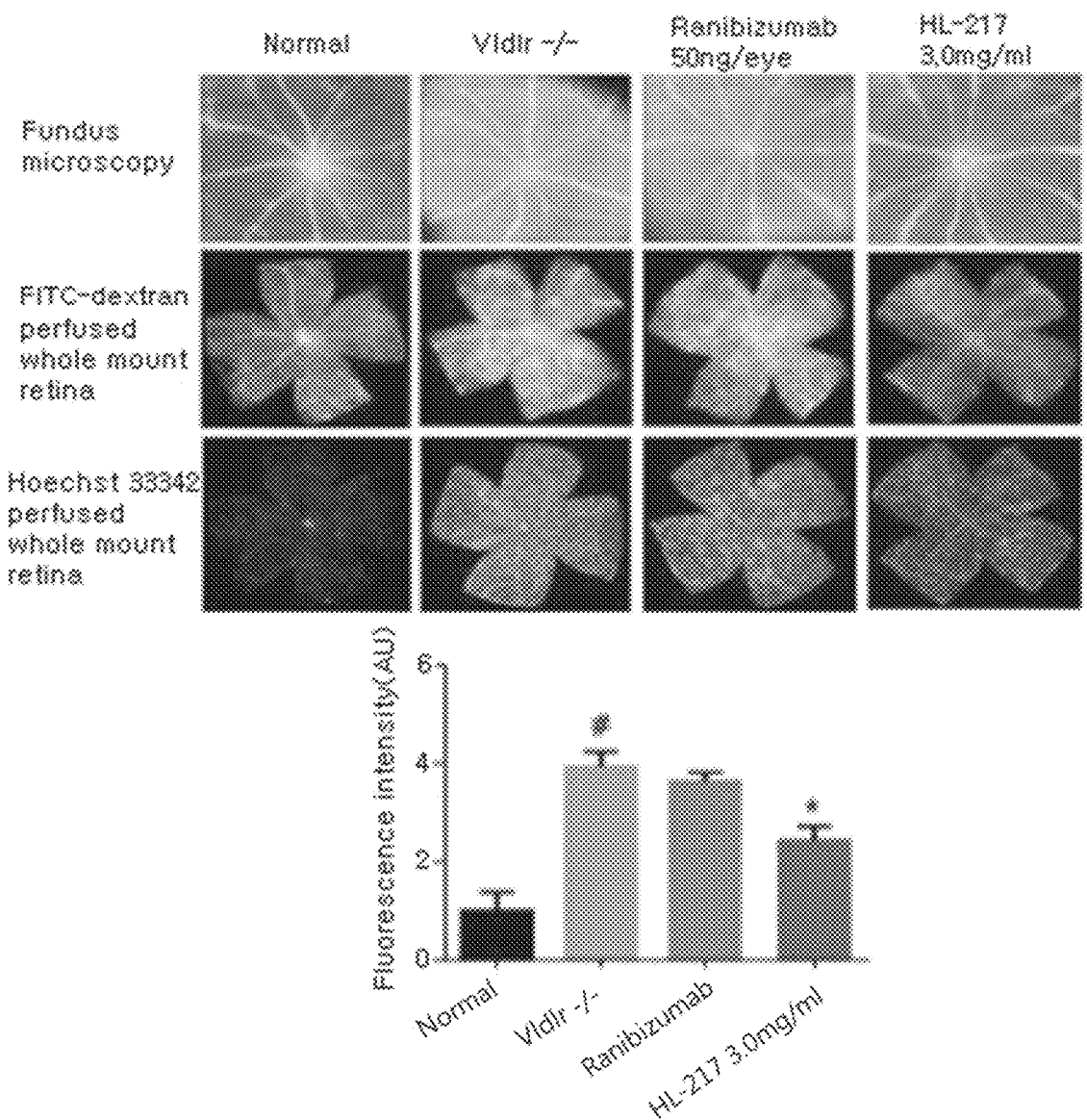
FIG. 1 shows the results obtained by evaluating the inhibitory efficacy against vascular leakage of the eye drop formulation of the present invention in an animal model of macular degeneration.

The present invention provides an eye drop formulation in the form of a solution, comprising (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof; propylene glycol as a stabilizing agent; and a pH controlling agent in an aqueous medium, wherein the eye drop formulation has a pH ranging from 4.0 to 5.0.

In the eye drop formulation of the present invention, the aqueous medium includes sterile water for injection, sterile purified water, physiological saline, etc.

In the eye drop formulation of the present invention, the (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran has the chemical structure of Formula 1, as described in the above. The pharmaceutically acceptable salt of the compound of Formula 1 may be in the form of an acid addition salt, an alkali metal salt, or an alkaline earth metal salt, disclosed in Korean Laid-open Patent Publication No. 10-2012-0112162, but not limited thereto. In the eye drop formulation of the present invention, the compound of Formula 1 may be present in a concentration of 3 mg/ml or more, preferably in a concentration ranging from 3 to 10 mg/ml.

It has been found by the present invention that, when formulation processes of the compound of Formula 1 are carried out using propylene glycol as a stabilizing agent, the stability of the resulting eye drop formulation can be remarkably improved. The propylene glycol may be present in a concentration ranging from 1 to 20 mg/ml, preferably in a concentration ranging from 5 to 17 mg/ml, more preferably in a concentration ranging from 10 to 15 mg/ml, particularly preferably in a concentration of about 13 mg/ml (i.e., in a concentration ranging from 12 to 14 mg/ml).

It has been also found by the present invention that, when the pH of the eye drop formulation in the form of a solution is controlled to a specific range (i.e., pH 4.0 to pH 5.0), the compound of Formula 1 can be dissolved in a high concentration, without the formation of precipitates. The eye drop formulation of the present invention may have preferably a pH ranging from 4.2 to 4.7, more preferably a pH of about 4.5 (i.e., a pH ranging from 4.4 to 4.6). The pH control may be carried out using a conventional pH controlling agent used in the field of an eye drop formulation, for example, hydrochloric acid and/or sodium hydroxide, but not limited thereto.

The eye drop formulation of the present invention may further comprise one or more excipients selected from the group consisting of an auxiliary stabilizing agent, a buffering agent, and a preservative. The amounts of the excipients may be appropriately selected by those skilled in the art, in consideration of the respective functions.

The auxiliary stabilizing agent may be one or more selected from the group consisting of ethylenediaminetetraacetic acid or a salt thereof (e.g., a sodium salt thereof) and tromethamine. For example, the auxiliary stabilizing agent may be used in an amount ranging from 0.05 to 10.0 mg/ml, but not limited thereto.

The buffering agent may be one or more selected from the group consisting of borax, boric acid, a phosphate salt (e.g., sodium phosphate, sodium hydrogen phosphate, potassium phosphate, etc.), citric acid, sodium citrate, and aminocaproic acid. For example, the buffering agent may be used in an amount ranging from 0.05 to 18.0 mg/ml, which depends on the kinds thereof.

The preservative may be one or more selected from the group consisting of benzalkonium chloride, chlorhexidine gluconate, chlorobutanol, sorbic acids (e.g., sorbic acid, potassium sorbate, sodium sorbate, etc.), and parabens (e.g., methylparaben, propylparaben, etc.). For example, the preservative may be used in an amount ranging from 0.01 to 0.5 mg/ml, but not limited thereto.

If necessary, the eye drop formulation of the present invention may be sterile-filtered with, for example, a bacterial filter such as a 0.2 μm membrane filter and then filled into an appropriate container.

In an embodiment, there is provided an eye drop formulation in the form of a solution comprising (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof; propylene glycol; ethylenediaminetetraacetic acid or a salt thereof; tromethamine; borax; boric acid; benzalkonium chloride; and a pH controlling agent in an aqueous medium, wherein the eye drop formulation has a pH ranging from 4.0 to 5.0.

In another embodiment, there is provided an eye drop formulation in the form of a solution comprising 3 to 10 mg/ml of (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof; 1 to 20 mg/ml of propylene glycol; 0.01 to 1.0 mg/ml of ethylenediaminetetraacetic acid or a salt thereof; 0.05 to 10.0 mg/ml of tromethamine; 1.0 to 11.0 mg/ml of borax; 0.1 to 18.0 mg/ml of boric acid; 0.01 to 0.5 mg/ml of benzalkonium chloride;

and a pH controlling agent in an aqueous medium, wherein the eye drop formulation has a pH ranging from 4.0 to 5.0.

In still another embodiment, there is provided an eye drop formulation in the form of a solution comprising 3 to 10 mg/ml of (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof; 10 to 15 mg/ml of propylene glycol; 0.5 mg/ml of ethylenediaminetetraacetic acid or a salt thereof; 0.35 mg/ml of tromethamine; 5.8 to 5.9 mg/ml of borax; 0.5 to 0.6 mg/ml of boric acid; 0.05 to 0.15 mg/ml of benzalkonium chloride; and a pH controlling agent in an aqueous medium, wherein the eye drop formulation has a pH ranging from 4.0 to 5.0.

The present invention also provides a pharmaceutical product for preventing or treating macular degeneration which is obtained by filling the eye drop formulation into a light-shielding container. Preferably, the pharmaceutical product for preventing or treating macular degeneration according to the present invention may be obtained by filling the eye drop formulation into a light-shielding container and then packing the resulting product in a paper case. The light-shielding container includes e.g., a non-transparent low-density polyethylene (LDPE) container and a non-transparent polypropylene (PP) container, but not limited thereto.

The present invention will be described in further detail with reference to the following examples. These examples are for illustrative purposes only and are not intended to limit the scope of the present invention.

In the following preparation examples, examples and experimental examples, HL217 means (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran.

Preparation Example 1: Evaluation of Manufacturability of the Eye Drop Formulation Having High Concentration The manufacturability of eye drop formulations in a solution form was evaluated by dissolving HL217 in the same manner, except for using the concentration of 0.3 w/v % (i.e., the concentration of 3.0 mg/ml) as the amount of HL217, in the eye drop solutions (0.06 w/v % and 0.09 w/v % eye drop solutions) disclosed in Formulation Examples 1 and 2 of Korean Laid-open Patent Publication No. 10-2012-0112162. That is, according to the components and amounts shown in Table 1, HL217, polyethylene glycol 400, glycerin, EDTA, and boric acid were added to the sterile purified water under stirring. The pH was adjusted to 6.5 with an aqueous hydrochloric acid solution and/or an aqueous sodium hydroxide solution; and then sterile purified water was added to the solution, so as to adjust the final volume. The amounts in Table 1 represent the amount of each component per 1 mL of the total volume.

TABLE 1

| Component | Preparation Example 1 (pH 6.5) |
|---|---|
| HL217 | 3.0 mg |
| Polyethylene glycol 400 | 150 mg |
| Glycerin | 120 mg |
| EDTA | 0.5 mg |
| Boric acid | 10 mg |

TABLE 1-continued

| Component | Preparation Example 1 (pH 6.5) |
|---|---|
| HCl | q.s. |
| NaOH | q.s. |
| Appearance | Precipitates generated |

As shown in the above, when the concentration of the active ingredient HL217 was increased to 3.0 mg/ml, the precipitates were generated and thus a solution was not prepared.

Preparation Example 2: Solubilization of HL217 and Stability Evaluation (1) Solubilization of HL217

In order to dissolve HL217 in the high concentration (in the concentration of 0.3 w/v % or more), various physicochemical factors were evaluated. Since the maximum allowable concentration of the U.S. Food and Drug Administration for polyethylene glycol 400 is 50 mg/ml in an eye drop formulation, the amount of polyethylene glycol 400 was adjusted to 1/10 (i.e., 15.0 mg) and correspondingly the amount of glycerin was also adjusted to 1/10 (i.e., 12.0 mg) for evaluating the solubilization of HL217. In the course of evaluating the effects of various physicochemical factors, it was found that the pH of the solution had a great influence on the solubilization of HL217. That is, when the pH was adjusted to a range of 4.5±0.5 among various factors, a transparent solution was obtained without generating precipitates. Specifically, according to the components and amounts shown in Table 2, HL217, polyethylene glycol 400, glycerin, EDTA, and boric acid were added to the sterile purified water under stirring. The pH was adjusted to 4.5 with an aqueous hydrochloric acid solution and/or an aqueous sodium hydroxide solution; and then sterile purified water was added to the solution, so as to adjust the final volume. The amounts in Table 2 represent the amount of each component per 1 mL of the total volume.

TABLE 2

| Component | Preparation Example 2-1 (pH 4.5) | Preparation Example 2-2 (pH 4.5) | Preparation Example 2-3 (pH 4.5) |
|---|---|---|---|
| HL217 | 3.0 mg | 3.0 mg | 3.0 mg |
| Polyethylene glycol 400 | 15.0 mg | — | 15.0 mg |
| Glycerin | 12.0 mg | 12.0 mg | 12.0 mg |
| EDTA | 0.5 mg | 0.5 mg | 0.5 mg |
| Boric acid | 10.0 mg | 10.0 mg | 10.0 mg |
| HCl | q.s. | q.s. | q.s. |
| NaOH | q.s. | q.s. | q.s. |
| Appearance | Transparent solution | Transparent solution | Transparent solution |

As can be seen from the results of Table 2, although the amounts of the auxiliary stabilizing agents (i.e., polyethylene glycol 400 and the glycerin) were 1/10 times, the transparent solutions were obtained without generating precipitates under the condition of pH 4.5.

(2) Stability Evaluation

The solutions of Preparation Examples 2-1, 2-2, and 2-3 were stored for 4 weeks under the refrigerated condition (5±3° C.), under the room temperature condition (25±2° C., 40±5% RH), and under the accelerated condition (40±2° C., 25% RH), respectively, so as to measure the amounts of degradation products. As the amounts of degradation products, the amounts of maximum degradation product and the amounts of total degradation products were measured by high performance liquid chromatography (HPLC) under the following conditions.

<HPLC Conditions>
Detector: UV/vis spectrophotometer (Wavelength: 254 nm)
Column: Luna C8 column (4.6*250 mm, 5 μm)
Flow rate: 1.0 mL/min
Injection volume: 20 μL
Mobile phase: ammonium formate buffer solution:acetonitrile=50:50 (the ammonium formate buffer solution was prepared by adjusting the pH of an ammonium formate solution (10 mM) to pH 5.5 with phosphoric acid.)
Column temperature: about 30° C.
Sample temperature: about 4° C.

The results obtained by measuring the amounts of degradation products as described in the above are shown in the following tables 3 to 5.

TABLE 3

Amounts of degradation products of the solution of Preparation Example 2-1

| Storage condition | | Initial | 2 weeks | 4 weeks |
|---|---|---|---|---|
| Refrigerated condition | Maximum degradation product | 0.32% | 0.99% | 1.24% |
| | Total degradation products | 0.38% | 1.61% | 1.80% |
| Room temperature condition | Maximum degradation product | 0.32% | 1.37% | 2.16% |
| | Total degradation products | 0.38% | 2.23% | 3.61% |
| Accelerated condition | Maximum degradation product | 0.32% | 2.14% | 2.61% |
| | Total degradation products | 0.38% | 3.33% | 4.00% |

TABLE 4

Amounts of degradation products of the solution of Preparation Example 2-2

| Storage condition | | Initial | 2 weeks | 4 weeks |
|---|---|---|---|---|
| Refrigerated condition | Maximum degradation product | Not detected | 0.65% | 1.08% |
| | Total degradation products | Not detected | 1.15% | 1.53% |
| Room temperature condition | Maximum degradation product | Not detected | 0.98% | 1.54% |
| | Total degradation products | Not detected | 1.56% | 2.85% |
| Accelerated condition | Maximum degradation product | Not detected | 1.75% | 2.54% |
| | Total degradation products | Not detected | 2.53% | 3.38% |

TABLE 5

Amounts of degradation products of the solution of Preparation Example 2-3

| Storage condition | | Initial | 2 weeks | 4 weeks |
|---|---|---|---|---|
| Refrigerated condition | Maximum degradation product | 0.36% | 1.10% | 1.35% |
| | Total degradation products | 0.42% | 1.10% | 1.71% |
| Room temperature condition | Maximum degradation product | 0.36% | 1.52% | 1.79% |
| | Total degradation products | 0.42% | 1.97% | 2.71% |
| Accelerated condition | Maximum degradation product | 0.36% | 2.54% | 3.01% |
| | Total degradation products | 0.42% | 3.78% | 4.36% |

As can be seen from the results of Tables 3 to 5, the solutions of Preparation Examples 2-1 to 2-3 show a significant increase in degradation products under all conditions after 2 weeks and 4 weeks, and thus are not suitable for the allowable level of degradation products (maximum degradation product: 1% or less, total degradation products: 2% or less).

Examples 1 and 2: Preparation of Stable Eye Drop Formulations in the Form of a Solution Containing HL217

(1) Preparation of Eye Drop Formulations in the Form of a Solution

In accordance with the components and amounts shown in Table 6, eye drop formulations in the form of a solution, which contain propylene glycol instead of polyethylene glycol/glycerin, were prepared. That is, according to the components and amounts shown in Table 6, HL217, propylene glycol, the stabilizing agent(s) (EDTA and/or tromethamine), the buffering agents (boric acid and borax) and benzalkonium chloride were added to the sterile purified water under stirring. The pH was adjusted to 4.5 with an aqueous hydrochloric acid solution and/or an aqueous sodium hydroxide solution; and then sterile purified water was added to the solution, so as to adjust the final volume. The amounts in Table 6 represent the amount of each component per 1 mL of the total volume.

TABLE 6

| Component | Example 1 (pH 4.5) | Example 2 (pH 4.5) |
|---|---|---|
| HL217 | 3.0 mg | 3.0 mg |
| Propylene glycol | 13.0 mg | 13.0 mg |
| EDTA | 0.5 mg | 0.5 mg |
| Tromethamine | — | 0.35 mg |
| Boric acid | 5.82 mg | 5.82 mg |
| Borax | 0.588 mg | 0.588 mg |
| Benzalkonium chloride | 0.1 mg | 0.1 mg |
| HCl | q.s. | q.s. |
| NaOH | q.s. | q.s. |
| Appearance | Transparent solution | Transparent solution |

(2) Stability Evaluation

The solutions of Examples 1 and 2 were stored for 4 weeks under the refrigerated condition (5±3° C.), under the room temperature condition (25±2° C., 40±5% RH), and under the accelerated condition (40±2° C., 25% RH), respectively, so as to measure the amounts of degradation products in the same manners as in (2) of Preparation Example 2. The results thereof are shown in the following tables 7 and 8.

TABLE 7

Amounts of degradation products of the solution of Example 1

| Storage condition | | Initial | 2 weeks | 4 weeks |
|---|---|---|---|---|
| Refrigerated condition | Maximum degradation product | Not detected | Not detected | 0.03% |
| | Total degradation products | Not detected | Not detected | 0.03% |
| Room temperature condition | Maximum degradation product | Not detected | 0.06% | 0.16% |
| | Total degradation products | Not detected | 0.09% | 0.21% |
| Accelerated condition | Maximum degradation product | Not detected | 0.34% | 0.79% |
| | Total degradation products | Not detected | 0.66% | 1.62% |

TABLE 8

Amounts of degradation products of the solution of Example 2

| Storage condition | | Initial | 2 weeks | 4 weeks |
|---|---|---|---|---|
| Refrigerated condition | Maximum degradation product | Not detected | Not detected | 0.04% |
| | Total degradation products | Not detected | Not detected | 0.04% |
| Room temperature condition | Maximum degradation product | Not detected | 0.07% | 0.18% |
| | Total degradation products | Not detected | 0.10% | 0.23% |
| Accelerated condition | Maximum degradation product | Not detected | 0.36% | 0.88% |
| | Total degradation products | Not detected | 0.64% | 1.60% |

As can be seen from the results of Tables 6 to 8, when using propylene glycol and adjusting the pH of the solution to pH 4.5, transparent solutions were obtained without generating precipitates and the generation of degradation products was remarkably decreased under all of the conditions (i.e., under the refrigerated condition, under the room temperature condition, and under the accelerated condition). Therefore, the eye drop formulations are suitable for the allowable level of degradation products (maximum degradation product: 1% or less, total degradation products: 2% or less). And also, the solution prepared by additionally adding tromethamine as a stabilizing agent showed a slight increase in stability under the accelerated condition, compared to the solution that tromethamine was not added, although there is no significance.

Examples 3 and 4: Preparation of Stable Eye Drop Formulations in the Form of a Solution Containing HL217

(1) Preparation of Eye Drop Formulations in the Form of a Solution

In accordance with the components and amounts shown in Table 9, eye drop formulations in the form of a solution were prepared. That is, the eye drop formulations in the form of a solution were prepared in the same manner as in Example 2, increasing the concentration of HL217 to 5.0 mg/ml and 10.0 mg/ml, respectively. The amounts in Table 9 represent the amount of each component per 1 mL of the total volume.

TABLE 9

| Component | Example 3 (pH 4.5) | Example 4 (pH 4.5) |
|---|---|---|
| HL217 | 5.0 mg | 10.0 mg |
| Propylene glycol | 13.0 mg | 13.0 mg |
| EDTA | 0.5 mg | 0.5 mg |
| Tromethamine | 0.35 mg | 0.35 mg |
| Boric acid | 5.82 mg | 5.82 mg |
| Borax | 0.588 mg | 0.588 mg |
| Benzalkonium chloride | 0.1 mg | 0.1 mg |
| HCl | q.s. | q.s. |
| NaOH | q.s. | q.s. |
| Appearance | Transparent solution | Transparent solution |

(2) Stability Evaluation

The solutions of Examples 3 and 4 were stored for 4 weeks under the refrigerated condition (5±3° C.), under the room temperature condition (25±2° C., 40±5% RH), and under the accelerated condition (40±2° C., 25% RH), respectively, so as to measure the amounts of degradation products in the same manners as in (2) of Preparation Example 2. The results thereof are shown in the following tables 10 and 11.

TABLE 10

Amounts of degradation products of the solution of Example 3

| Storage condition | | Initial | 2 weeks | 4 weeks |
|---|---|---|---|---|
| Refrigerated condition | Maximum degradation product | Not detected | 0.03% | 0.04% |
| | Total degradation products | Not detected | 0.03% | 0.04% |
| Room temperature condition | Maximum degradation product | Not detected | 0.08% | 0.16% |
| | Total degradation products | Not detected | 0.10% | 0.22% |
| Accelerated condition | Maximum degradation product | Not detected | 0.35% | 0.79% |
| | Total degradation products | Not detected | 0.67% | 1.63% |

TABLE 11

Amounts of degradation products of the solution of Example 4

| Storage condition | | Initial | 2 weeks | 4 weeks |
|---|---|---|---|---|
| Refrigerated condition | Maximum degradation product | Not detected | 0.03% | 0.04% |
| | Total degradation products | Not detected | 0.07% | 0.05% |
| Room temperature condition | Maximum degradation product | Not detected | 0.07% | 0.15% |
| | Total degradation products | Not detected | 0.10% | 0.23% |
| Accelerated condition | Maximum degradation product | Not detected | 0.33% | 0.89% |
| | Total degradation products | Not detected | 0.62% | 1.71% |

As can be seen from the results of Tables 9 to 11, when using propylene glycol and adjusting the pH of the solution to pH 4.5, transparent solutions containing HL217 in the high concentrations (e.g., 10 mg/ml) were obtained and are suitable for the allowable level of degradation products (maximum degradation product: 1% or less, total degradation products: 2% or less) under all of the conditions (i.e., under the refrigerated condition, under the room temperature condition, and under the accelerated condition).

Examples 5 to 7: Preparation of Stable Eye Drop Formulations in the Form of a Solution Containing HL217

(1) Preparation of Eye Drop Formulations in the Form of a Solution

In accordance with the components and amounts shown in Table 12, eye drop formulations in the form of a solution were prepared. That is, the eye drop formulations in the form of a solution were prepared in the same manner as in Example 2, changing the concentration of propylene glycol to 1.0 mg/ml, 5.0 mg/ml and 20.0 mg/ml, respectively. The amounts in Table 12 represent the amount of each component per 1 mL of the total volume.

TABLE 12

| Component | Example 5 (pH 4.5) | Example 6 (pH 4.5) | Example 7 (pH 4.5) |
|---|---|---|---|
| HL217 | 3.0 mg | 3.0 mg | 3.0 mg |
| Propylene glycol | 1.0 mg | 5.0 mg | 20.0 mg |
| EDTA | 0.5 mg | 0.5 mg | 0.5 mg |
| Tromethamine | 0.35 mg | 0.35 mg | 0.35 mg |
| Boric acid | 5.82 mg | 5.82 mg | 5.82 mg |
| Borax | 0.588 mg | 0.588 mg | 0.588 mg |
| Benzalkonium chloride | 0.1 mg | 0.1 mg | 0.1 mg |
| HCl | q.s. | q.s. | q.s. |
| NaOH | q.s. | q.s. | q.s. |
| Appearance | Transparent solution | Transparent solution | Transparent solution |

(2) Stability Evaluation

The solutions of Examples 5 to 7 were stored for 4 weeks under the refrigerated condition (5±3° C.), under the room temperature condition (25±2° C., 40±5% RH), and under the accelerated condition (40±2° C., 25% RH), respectively, so as to measure the amounts of degradation products in the same manners as in (2) of Preparation Example 2. The results thereof are shown in the following tables 13 to 15.

TABLE 13

Amounts of degradation products of the solution of Example 5

| Storage condition | | Initial | 2 weeks | 4 weeks |
|---|---|---|---|---|
| Refrigerated condition | Maximum degradation product | Not detected | Not detected | Not detected |
| | Total degradation products | Not detected | Not detected | Not detected |
| Room temperature condition | Maximum degradation product | Not detected | 0.07% | 0.16% |
| | Total degradation products | Not detected | 0.09% | 0.21% |
| Accelerated condition | Maximum degradation product | Not detected | 0.35% | 0.87% |
| | Total degradation products | Not detected | 0.64% | 1.66% |

TABLE 14

Amounts of degradation products of the solution of Example 6

| Storage condition | | Initial | 2 weeks | 4 weeks |
|---|---|---|---|---|
| Refrigerated condition | Maximum degradation product | Not detected | Not detected | Not detected |
| | Total degradation products | Not detected | Not detected | Not detected |
| Room temperature condition | Maximum degradation product | Not detected | 0.06% | 0.16% |
| | Total degradation products | Not detected | 0.09% | 0.22% |
| Accelerated condition | Maximum degradation product | Not detected | 0.34% | 0.79% |
| | Total degradation products | Not detected | 0.64% | 1.57% |

TABLE 15

Amounts of degradation products of the solution of Example 7

| Storage condition | | Initial | 2 weeks | 4 weeks |
|---|---|---|---|---|
| Refrigerated condition | Maximum degradation product | Not detected | Not detected | Not detected |
| | Total degradation products | Not detected | Not detected | Not detected |
| Room temperature condition | Maximum degradation product | Not detected | 0.08% | 0.16% |
| | Total degradation products | Not detected | 0.14% | 0.20% |
| Accelerated condition | Maximum degradation product | Not detected | 0.33% | 0.83% |
| | Total degradation products | Not detected | 0.62% | 1.56% |

As can be seen from the results of Tables 12 to 15, when using propylene glycol in the concentrations of 1 mg/ml to 20 mg/ml, transparent solutions were obtained without generating precipitates and are suitable for the allowable level of degradation products (maximum degradation product: 1% or less, total degradation products: 2% or less) under all of the conditions (i.e., under the refrigerated condition, under the room temperature condition, and under the accelerated condition).

Experimental Example 1: Photostability Test

The photostability of the eye drop formulation was evaluated using a transparent low-density polyethylene (LDPE) container [PurellPE1810E natural (GERRESHEIMER)] as a transparent container, a non-transparent low-density polyethylene container [PurellPE1810E white (GERRESHEIMER)] as a non-transparent container, and a paper case, respectively. That is, the eye drop formulation prepared in Example 2 was stored under the storage conditions of the following table 16. Each test group was placed in a photo chamber and then exposed to ultraviolet light for 40 hours under the condition of 5 w/m$^2$ or exposed to visible light for 40 hours under the condition of 30000 lux/hr. After the exposure for 40 hours, the amounts of degradation products were measured in the same manners as in (2) of Preparation Example 2. The results thereof are shown in the following table 17.

TABLE 16

| | Storage condition |
|---|---|
| Test Group 1 | The eye drop formulation of Example 2 was stored in a transparent LDPE container. |

TABLE 16-continued

| | Storage condition |
|---|---|
| Test Group 2 | The eye drop formulation of Example 2 was stored in a non-transparent LDPE container. |
| Test Group 3 | The eye drop formulation of Example 2 was filled in a transparent LDPE container and then stored in a paper case. |
| Test Group 4 | The eye drop formulation of Example 2 was filled in a non-transparent LDPE container and then stored in a paper case. |

TABLE 17

| | Ultraviolet light | | | | Visible light | | | |
|---|---|---|---|---|---|---|---|---|
| | Test Group 1 | Test Group 2 | Test Group 3 | Test Group 4 | Test Group 1 | Test Group 2 | Test Group 3 | Test Group 4 |
| Maximum degradation product | 0.30% | 0.10% | 0.03% | 0.03% | 0.72% | 0.03% | 0.03% | 0.03% |
| Total degradation products | 1.11% | 0.13% | 0.03% | 0.06% | 3.43% | 0.04% | 0.06% | 0.04% |

As can be seen from the results of Table 17, It is preferred that the HL217-containing eye drop formulation is filled in a non-transparent container; and it is more preferable that the HL217-containing eye drop formulation is filled in a non-transparent container and then stored in a paper case.

Experimental Example 2: Efficacy Tests in Animals

The efficacies against macular degeneration were demonstrated using the mice with very low-density lipoprotein receptor (vldlr) gene knockout (C57Bl/6 mice, Jackson Laboratory, USA) as an animal model of age-related macular degeneration (AMD). Lucentis™ injection (Norvatis, Basel, Switzerland) was used as a positive control.

The control group was instilled with 1 drop of sterile physiological saline, in each eye of normal mice (n=8), twice daily for 3 weeks. The AMD-induced group was instilled with 1 drop of sterile physiological saline, in each eye of mice with vldlr gene knockout (vldlr −/− mice), twice daily for 3 weeks. The positive control group received 1 μl of Lucentis™ injection (containing 50 ng/μl of ranibizumab) in each eye of vldlr −/− mice, by a single intravitreal administration using a Hamiltion syringe (Hamilton company, Reno, NV, USA). The test group was instilled with 1 drop of the eye drop formulation of Example 2, in each eye of vldlr −/− mice, twice daily for 3 weeks.

The following experiments were carried out In order to evaluate any abnormality of retinal blood vessels, such as angiogenesis formation and abnormal blood vessel permeability. At necropsy, anesthesia was induced by intraperitoneal injection of 10 mg/kg of zolazepam (Zoletil, Virbac, Carros, France) and 10 mg/kg of xylazine hydrochloride (Rumpun, Bayer, Frankfurt, Germany). The abdominal cavity and thoracic cavity were incised to secure the heart; and then 50 mg/mL of fluorescein-dextran (10 Kda molecular weight, Sigma, St. Louis, MO, USA) and 10 mg/mL of Hoechst 33342 (Sigma) in sterile PBS (1 mL) were injected into the left ventricle. After 10 minutes, the eye was extracted and fixed in 4% paraformaldehyde for 2 hours to isolate the retina. The isolated retina was placed on a slide, dropped with an aqueous mounting medium (Fluoromount™, Sigma, St. Louis, MO, USA) and then observed under a fluorescence microscope. For quantitative analysis of tracer dye, blood was collected from the heart 10 minutes after the dye injection, perfused with sterile PBS to remove residual dye from the blood vessels, and then the eyes were extracted to isolate the retina. The isolated retina was homogenized with 100 μL of PBS and then centrifuged to obtain the supernatant, in which the amount of FITC-dextran was then measured using a spectrofluorophotometer. The fluorescence intensity was measured under the conditions of 485 nm of excitation and 530 nm of emission; and calculated with calibrating the FITC fluorescence values and retinal protein concentrations in the blood. The results thereof are shown in FIG. 1.

In addition, the following experiments were carried out to evaluate subretinal angiogenesis. The isolated retinal tissue was fixed with 4% paraformaldehyde for 1 hour and then reacted with Alexa Fluor 594-conjugated Griffonia *bandeiraea simplicifolia* isolectin B4 (IB4 Alexa Fluor 594, 1:100 dilution; Molecular probes, USA) for 2 hours. After washing sufficiently with PBS, the retinal tissue was placed on a slide and then dropped with an aqueous mounting medium (Fluoromount™, Sigma, St. Louis, MO, USA). After sufficiently drying, the resultant was observed under a fluorescence microscope and photographed. The retinal section was subject to H&E staining and then subretinal neovascularization was analyzed using the ImageJ software (National Institutes of Health, Bethesda, MD, USA). The results thereof are shown in FIG. 2.

As shown in FIG. 1, in normal mice, the border of the blood vessels was clear and normal vascular integrity was well-maintained. However, in vldlr −/− mice, the fluorescent tracer dye injected into the blood vessels was leaked out of the blood vessels (white arrow) to increase the fluorescence intensity of the retina. In addition, the Hoechst 33342 staining material, which exhibits blue fluorescence, was also leaked out of the blood vessels and thus numerous findings of vascular leakage were observed; and subretinal neovascularization areas (red arrow) were observed. However, in the eyes treated with the eye drop formulation of Example 2, the vascular leakage and pathogenic angiogenesis were inhibited. The positive control group showed significant efficacy only at the 2nd week of drug administration.

Figure 2:
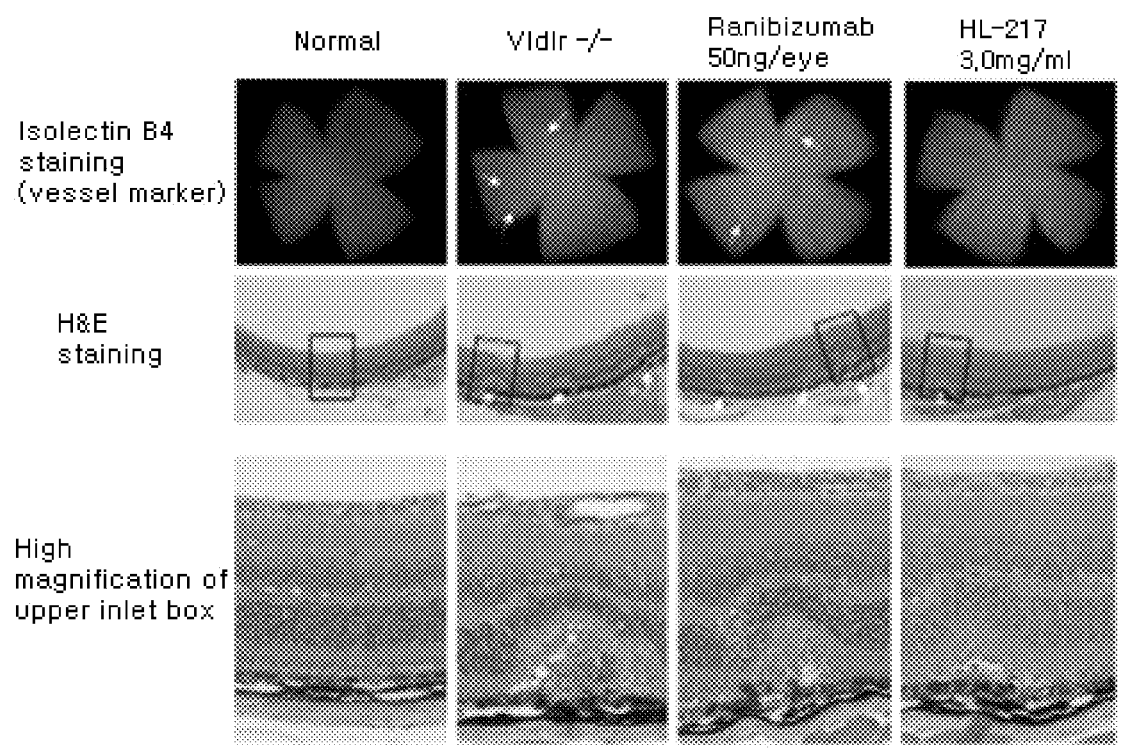
FIG. 2 shows the results obtained by evaluating the inhibitory efficacy against pathogenic retinal angiogenesis of the eye drop formulation of the present invention in an animal model of macular degeneration.

As can be seen From FIG. 2, in case of isolectin B4 staining analyses, the vldlr−/− mice showed subretinal neovascular tufts (white arrow) in several scattered places but the area thereof was decreased by administration of the eye drop formulation of Example 2. In addition, in the H&E staining analyses of retinal sections, the vldlr−/− mice showed numerous abnormal neovascularizations in the subretinal area (arrow area), which was decreased by administration of the eye drop formulation of Example 2.

The invention claimed is:

1. An eye drop formulation in the form of a solution, comprising (2R,3R,4S)-6-amino-4-N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof; propylene glycol as a stabilizing agent; and a pH controlling agent in an aqueous medium, wherein the eye drop formulation has a pH ranging from 4.0 to 5.0.

2. The eye drop formulation according to claim 1, wherein the (2R,3R,4S)-6-amino-4-N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof is present in a concentration of 3 mg/ml or more.

3. The eye drop formulation according to claim 1, wherein the (2R,3R,4S)-6-amino-4-N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof is present in a concentration ranging from 3 to 10 mg/ml.

4. The eye drop formulation according to claim 1, wherein the propylene glycol is present in a concentration ranging from 1 to 20 mg/ml.

5. The eye drop formulation according to claim 1, wherein the propylene glycol is present in a concentration ranging from 5 to 17 mg/ml.

6. The eye drop formulation according to claim 1, wherein the propylene glycol is present in a concentration ranging from 10 to 15 mg/ml.

7. The eye drop formulation according to claim 1, wherein the eye drop formulation has a pH ranging from 4.2 to 4.7.

8. The eye drop formulation according to claim 1, wherein the eye drop formulation has a pH of about 4.5.

9. The eye drop formulation according to claim 1, further comprising one or more excipients selected from the group consisting of an auxiliary stabilizing agent, a buffering agent, and a preservative.

10. The eye drop formulation according to claim 9, wherein the auxiliary stabilizing agent is one or more selected from the group consisting of ethylenediaminetetraacetic acid or a salt thereof and tromethamine.

11. The eye drop formulation according to claim 9, wherein the buffering agent is one or more selected from the group consisting of borax, boric acid, a phosphate salt, citric acid, sodium citrate, and aminocaproic acid.

12. The eye drop formulation according to claim 9, wherein the preservative is one or more selected from the group consisting of benzalkonium chloride, chlorhexidine gluconate, sorbic acids, chlorobutanol, and parabens.

13. The eye drop formulation according to claim 1, comprising (2R,3R,4S)-6-amino-4-N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof; propylene glycol; ethylenediaminetetraacetic acid or a salt thereof; tromethamine; borax; boric acid; benzalkonium chloride; and a pH controlling agent in an aqueous medium.

14. The eye drop formulation according to claim 1, comprising 3 to 10 mg/ml of (2R,3R,4S)-6-amino-4-N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof; 1 to 20 mg/ml of propylene glycol; 0.01 to 1.0 mg/ml of ethylenediaminetetraacetic acid or a salt thereof; 0.05 to 10.0 mg/ml of tromethamine; 1.0 to 11.0 mg/ml of borax; 0.1 to 18.0 mg/ml of boric acid; 0.01 to 0.5 mg/ml of benzalkonium chloride; and a pH controlling agent in an aqueous medium.

15. The eye drop formulation according to claim 1, comprising 3 to 10 mg/ml of (2R,3R,4S)-6-amino-4-N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt thereof; 10 to 15 mg/ml of propylene glycol; 0.5 mg/ml of ethylenediaminetetraacetic acid or a salt thereof; 0.35 mg/ml of tromethamine; 5.8 to 5.9 mg/ml of borax; 0.5 to 0.6 mg/ml of boric acid; 0.05 to 0.15 mg/ml of benzalkonium chloride; and a pH controlling agent in an aqueous medium.

16. A pharmaceutical product for preventing or treating macular degeneration which is obtained by filling the eye drop formulation according to claim 1, into a light-shielding container.

17. A pharmaceutical product for preventing or treating macular degeneration according to claim 16, wherein the pharmaceutical product is obtained by filling the eye drop formulation into a light-shielding container and then packing the resulting product in a paper case.

* * * * *